US006972020B1

(12) United States Patent
Grayson et al.

(10) Patent No.: US 6,972,020 B1
(45) Date of Patent: Dec. 6, 2005

(54) MULTI-DIRECTIONAL INTERNAL DISTRACTION OSTEOGENESIS DEVICE

(75) Inventors: Barry Grayson, New York, NY (US); Bruno Vendittelli, Toronto (CA); Joseph McCarthy, Englewood, NJ (US); Matthew Harrow, Jacksonville, FL (US); Brian Schumacher, Jacksonville, FL (US)

(73) Assignee: New York University, New York, NY (US)

( * ) Notice: Subject to any disclaimer, the term of this patent is extended or adjusted under 35 U.S.C. 154(b) by 79 days.

(21) Appl. No.: 10/159,269

(22) Filed: Jun. 3, 2002

Related U.S. Application Data

(60) Provisional application No. 60/294,640, filed on Jun. 1, 2001.

(51) Int. Cl.[7] .............................................. A61B 17/58
(52) U.S. Cl. ......................................................... 606/90
(58) Field of Search .............................. 606/69, 70, 71, 606/90, 86, 105

(56) References Cited

U.S. PATENT DOCUMENTS 5,681,313 A * 10/1997 Diez ........................... 606/69
6,277,124 B1 * 8/2001 Haag ........................... 606/105
6,383,189 B1 * 5/2002 Schumacher ................. 606/86
6,471,706 B1 * 10/2002 Schumacher et al. ......... 606/69
2002/0156485 A1 * 10/2002 Sellers et al. ................ 606/105

OTHER PUBLICATIONS

U.S. Appl. No. 60/237,519, filed Oct. 4, 2000; Sellers, Timothy.*

* cited by examiner

Primary Examiner—Eduardo C. Robert
(74) Attorney, Agent, or Firm—Browdy and Neimark, PLLC

(57) ABSTRACT

The present invention provides an improved orthopedic system for the modification of the distance between the maxilla and zygoma. In a preferred embodiment, the system includes proximal and distal footplates attached to an orthopedic device. The distal footplate is attached to the zygoma, with the proximal footplate being mechanically coupled to the maxilla. This mechanical coupling is achieved either through attachment directly to the maxilla or by attachment to a construct which is then wired to the patient's teeth. The orthopedic device, which may be a distractor, allows for modification of the distance between the maxilla and zygoma. The entire system can advantageously be placed intra-orally within a patient. In a preferred embodiment, the footplates are also detachable from the orthopedic device and are composed of a bioresorbable material, such that they will be absorbed by the patient's body. Methods for using this novel orthopedic system are also disclosed.

27 Claims, 10 Drawing Sheets

MULTI-DIRECTIONAL INTERNAL DISTRACTION OSTEOGENESIS DEVICE

CROSS-REFERENCE TO RELATED APPLICATION

This application claims priority rights from U.S. Provisional Application 60/294,640, filed Jun. 1, 2001.

BACKGROUND OF THE INVENTION

The present invention relates generally to a bone distractor device and more particularly, to a bone distractor device having multiple degrees of freedom.

Conventional bone distractor devices utilize plates fixed to different bone areas, a transport bone segment, and a fixed bone area. The transport bone segment is attached to a linear device that allows the transport bone segment to be moved along a linear path, resulting in the generation or distraction of a linear bone segment. When a bone segment is to be distracted in other than the direction in which the distractor device is connected, the distraction device usually must be removed and reattached, requiring additional medical procedures. The present invention was developed in light of these drawbacks.

BRIEF SUMMARY OF THE INVENTION

A bone distractor for distracting bone tissue includes a first bone attachment portion, a second bone attachment portion, and a linkage connecting the first bone attachment portion with the second bone attachment portion. The linkage allows at the first or second bone attachment portion to move with respect to the other along a linear path. The linkage allows the first or second bone attachment portions to rotationally move with respect to the other.

In another aspect of the invention, the first bone attachment portion and second bone attachment portion are interorally positioned on a mandible of a human jaw. Skin may generally cover the first bone attachment portion and/or second attachment portion.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

Figure 1A:
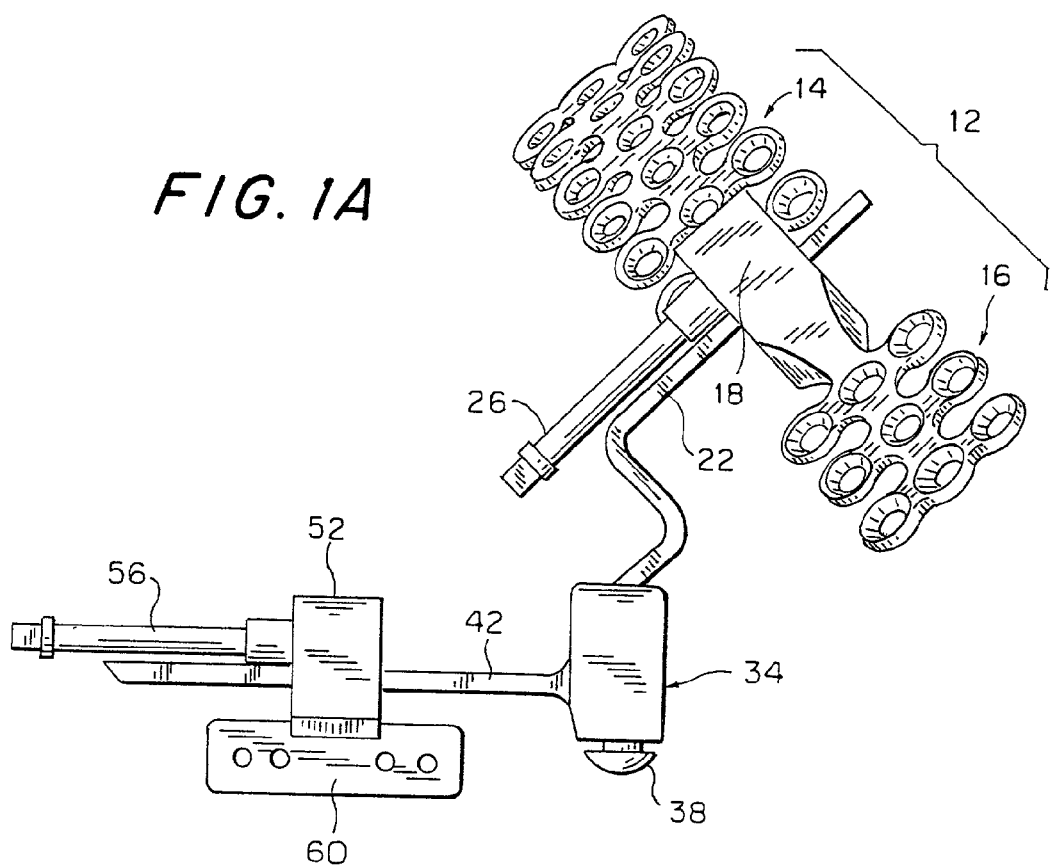
FIGS. 1A, 1B, 1C, and 1D, are, respectively, a side elevational view in a first operating position, a front perspective view in the first operating position, a side elevational view in a second operating position and a top plan view in the second operating position of a first preferred embodiment of a device according the present invention.

A first preferred embodiment of the invention is illustrated in FIGS. 1A–1D, which will be described together.

This embodiment includes an upper plate 12 composed of two wings 14 and 16. Plate 12 is secured to, and forms a unit with, an upper housing 18. All of the components of the device illustrated in FIGS. 1A–1D may be made of metal and wings 14 and 16 and housing 18 may be formed as a single cast unit, or wings 14 and 16 may be formed separately from housing 18 then welded to the side of walls of housing 18. An upper drive track 22 extends through a passage in housing 18. This passage may be formed directly in the cast unit constituting housing 18. A shaft 26 carries a threaded element (not visible) that also extends into the opening in housing 18. The threaded end of shaft 26 engages threading, or teeth, 28 on track 22 in such a manner that rotation of shaft 26 will produce movement of housing 18 along the length of track 22. Thus, track 22 cooperates with the threaded element to form a worm screw rack mechanism. The internal structure of housing 18 will be described in further detail below.

A rotational adjustment gear housing 34 contains a gear wheel that is coupled to the lower end of track 22 and a screw 38 having threads that engage the gear wheel. Rotation of screw 38 produces a rotation of the gear wheel, and a corresponding pivotal movement of track 22, for example between the position shown in FIGS. 1A and 1B, on one hand, and the position shown in FIGS. 1C and 1D, on the other hand. The structure within housing 34 will be described in greater detail below.

In the illustrated embodiment, track 22 has two successive bent portions that extend at right angles to one another. Track 22 has a lower end mounted in housing 34. These portions serve to offset the upper portion of track 22, along which housing 18 can be displaced, from the axis of rotation of the gear wheel, so that the upper portion of track 22 extends along a line that will intersect a lower drive track 42 at a point between the proximal and distal ends of track 42.

A lower drive track 42 is rigidly fixed to housing 34 and carries, at its upper surface in the figures, a threading, or teeth, 46 similar to threading 28. Drive track 42 extends through an opening in a lower housing 52. This opening further receives the threaded end of second shaft 56, which threaded end engages threading 46. Rotation of shaft 56 effects a movement of housing 52 along track 42. The mechanism within housing 52 is identical to that within housing 18 and will be described in greater detail below.

Secured to housing 52, below drive track 46, is an anterior lower plate 60 provided with a plurality of bone screw holes 62.

Figure 1B:
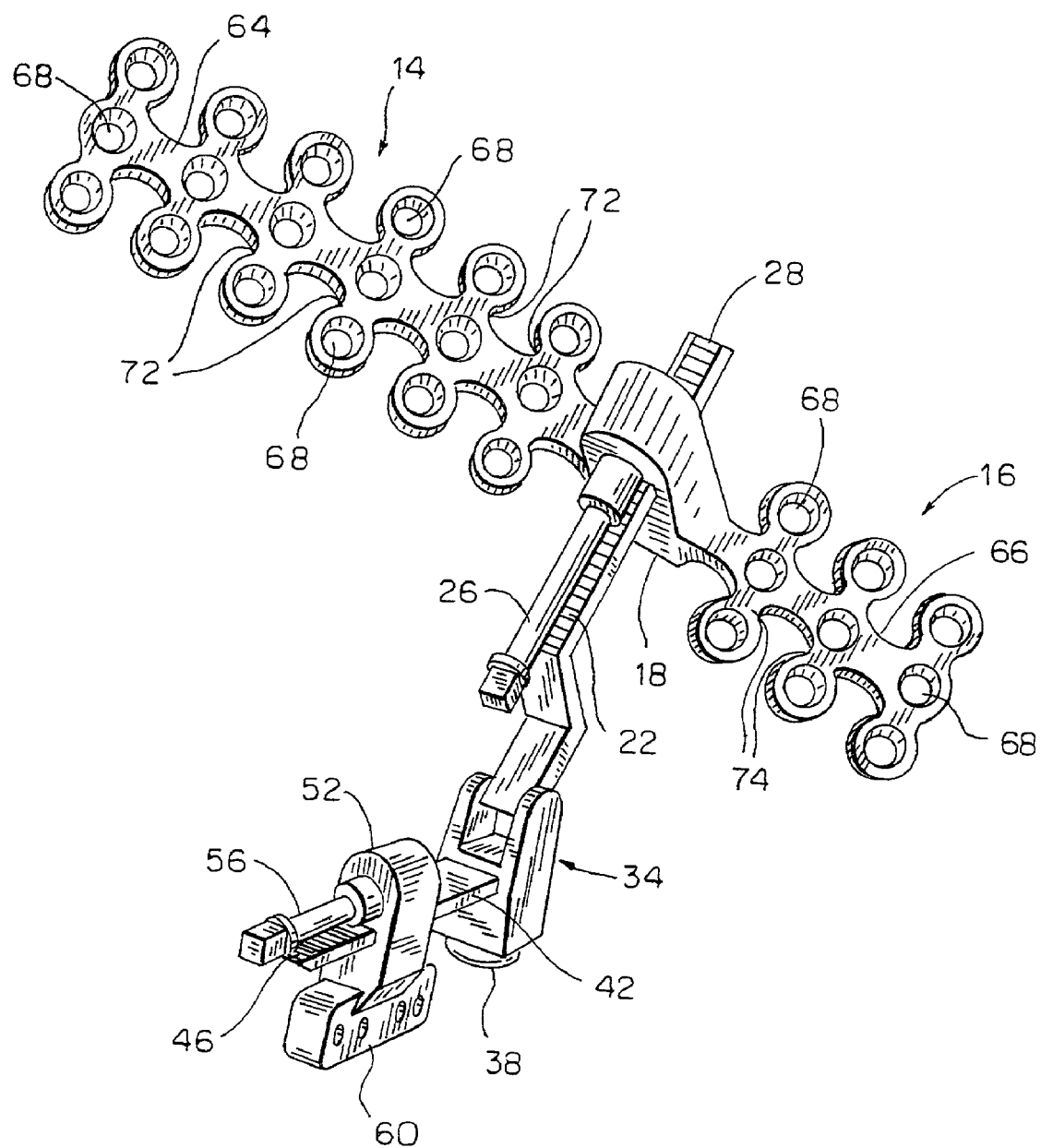

Referring specifically to FIG. 1B, each wing 14, 16 of upper plate 12 is composed of a longitudinal strip 64, 66 provided with a plurality of bone screw holes 68. Extensions 72, 74 extend laterally from either side of each strip 64, 66 and each extension 72, 74 is provided with at least one bone screw hole 68. Depending on the exact conformations of the bone regions to which wings 14 and 16 are to be secured, one or more of extensions 72, 74 of each wing can be broken off prior to implantation.

Figure 1C:
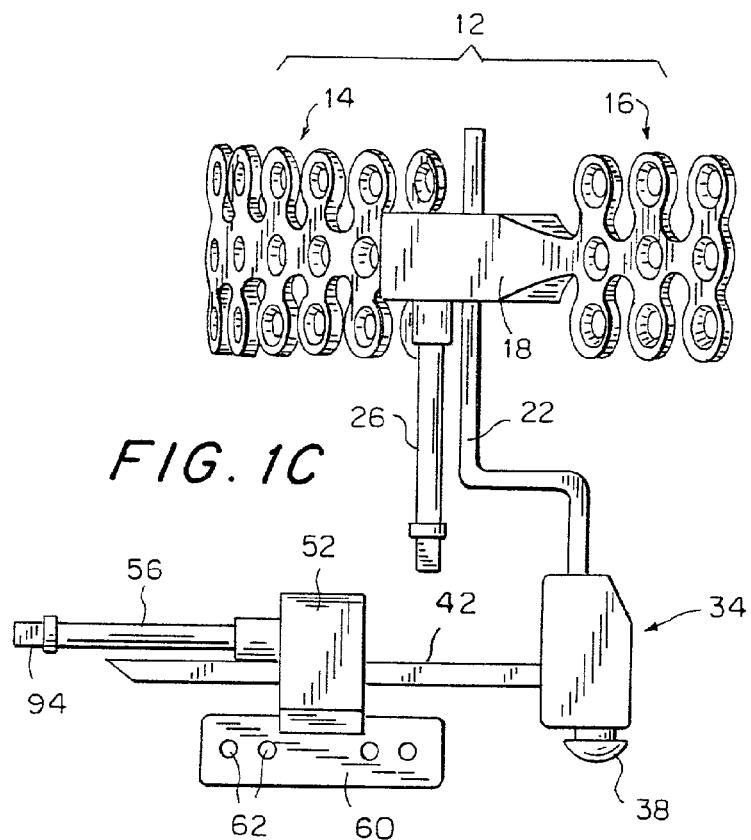
Figure 1D:
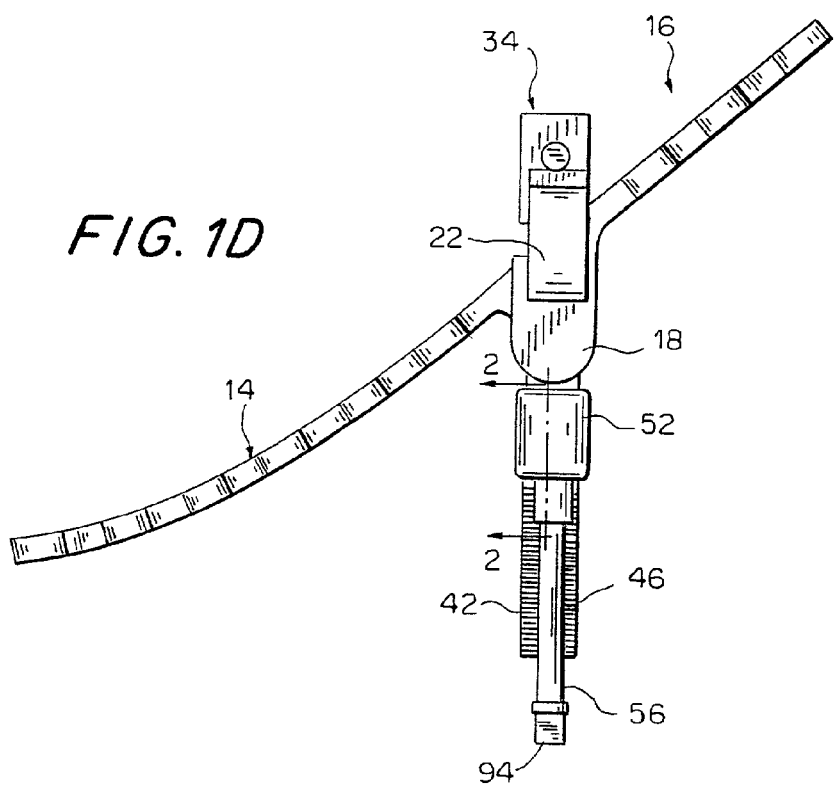

As shown particularly in the top plan view of FIG. 1D, wings 14 and 16 extend from housing 18 along a plane that is inclined with respect to the longitudinal axis of track 42 and shaft 56, and wing 14 is initially given a curved configuration. These orientation features of wings 14 and 16 are selected to conform to the facial skeleton portions to which wings 14 and 16 are to be attached for an individual having an average facial skeleton conformation. Models having different dimensions may be produced for pediatric patients, on the one hand, and adult patients, on the other. Since there will be variations in conformation from one individual to another, wings 14 and 16 are made of a material that is capable of being bent to conform to the individual patient.

Figure 1E:
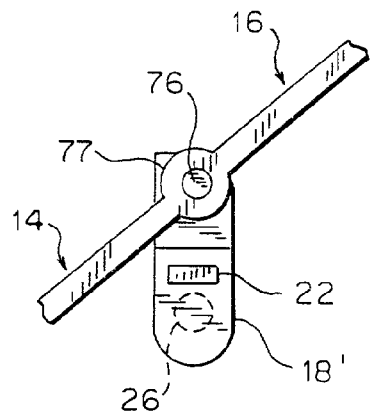
FIG. 1E is a top plan, detail view of a modified version of a component of the device of FIGS. 1A–1D.
Figure 1F:
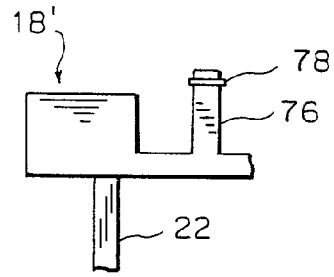
FIG. 1F is a side elevational, detail view of the component shown in FIG. 1E.

In the embodiment shown in FIGS. 1A–1D, wings 14 and 16 form a one-piece unit with housing 18. However, according to an alternative embodiment shown in FIGS. 1E and 1F, wings 14 and 16 may be formed as a one-piece unit separate from a housing 18'. Here, housing 18' still receives track 22 and shaft 26, but is provided with a plate portion 75 carrying an upstanding pin 76. The unit providing wings 14 and 16 has a cylindrical portion 77 presenting a through bore that seats over pin 76. Pin 76 may be provided at its upper end with a retaining member 78, such as a locking clip, to hold portion 77 in place on pin 76. With this arrangement the unit that includes wings 14 and 16 and portion 77 can be rotated around pin 76 to facilitate positioning wings 14 and 16 relative to the bone surface to which they are to be secured. Wings 14 and 16 and portion 77 are not shown in FIG. 1F to allow the form of housing 18' to be viewed more clearly.

Figure 2A:
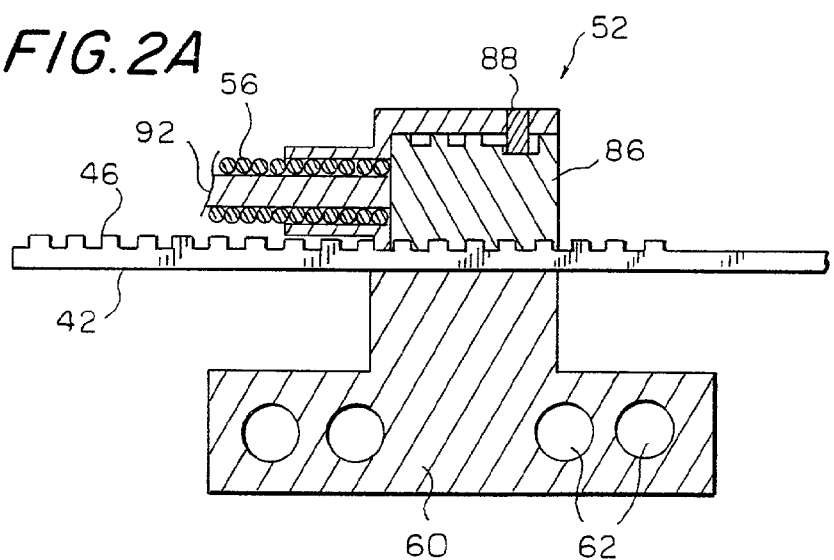
FIG. 2A is cross-sectional view taken along line 2—2 of FIG. 1D, showing a worm screw rack displacement mechanism.

FIG. 2A is a cross-sectional view taken along line 2—2 of FIG. 1D. As stated above, housing 52 is provided with an opening, or through bore, that receives a screw, or threaded element, 86 having a male thread that is configured to mate with threading 46 on drive track 42. Screw 86 has a free end provided with an annular recess into which is inserted a retaining pin 88 to prevent longitudinal movement of screw 86 relative to housing 52, while allowing screw 86 to rotate within the opening provided in housing 52. The opposite end of screw 86 is secured to the distal end of shaft 56.

As further illustrated in FIG. 2A, shaft 56 may be composed of a tightly wound wire coil enclosing a core 92 that may be rigid or bendable. Core 92 can be a solid rod or a stranded, twisted wire capable of applying tensile forces to thread 86 and housing 52. By making shaft 56 deformable, it can be bent to conform to the portion of the patient's oral cavity in which the device is installed, thus promoting wearer comfort.

As shown in FIGS. 1A–1D, the outer, or proximal, end of shaft 56 may be provided with a square head 94 that is engageable with a socket of a hand tool to allow shaft 56 to be rotated. When shaft 56 is rotated, screw 86 is rotated along therewith so that the engagement of the threads on screw 86 with threading 46 causes relative longitudinal movement between housing 52 and plate 60, on the one hand, and track 42, on the other hand.

Housing 18 may have the same internal structure as housing 52, and shaft 26 may be identical to shaft 56.

Figure 2B:
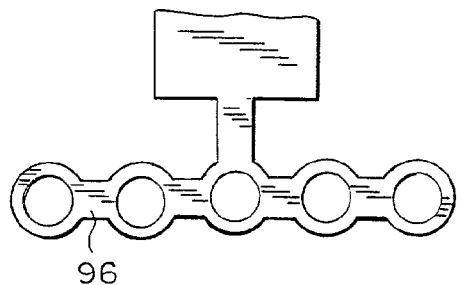
FIG. 2B is a side elevational detail view of a modified form of construction of a portion of the structure shown in FIG. 2A.

In the embodiment shown in FIGS. 1A–1D and 2A, plate 60 is not bendable, or is only slightly bendable. Alternatively, as shown in FIG. 2B, plate 60 can be replaced by a malleable bone screw plate 96 provided with bone screw holes. Plate 96 can be fabricated according to principles known in the art to be sufficiently malleable to allow the plate to by bent manually to surface where it is to be affixed. This may be a bone surface or, as will be described below, a surface of a surgical fixation splint.

As will be described in greater detail below, the device according to the invention will be implanted internally, so that shafts 26 and 56, as well as housings 34 and 52 and tracks 22 and 42 will be located within the patient's mouth or oral cavity. When implanted, housing 18, 18' can be located above the oral mucosa (submucosa) against the anterior surface of the zygomatic buttress.

Figure 3:
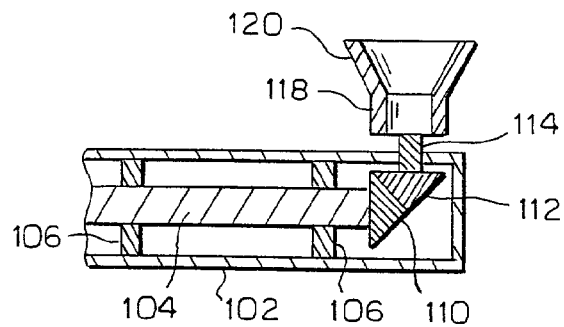
FIG. 3 is a cross-sectional, detail view of the distal end of a tool used for adjusting the device of FIGS. 1A–1D.

When housing 18 is to be displaced along track 22, shaft 26 can be rotated with the aid of a special tool having an operating end that may have the form shown in FIG. 3. This tool may include a handle (not shown) and a housing 102 that extends to a point at which it can be grasped by the person making the adjustment. The handle is secured to a shaft 104 that is rotatably mounted in bearings 106 mounted within housing 102. The free, or distal end of shaft 104 is secured to a first bevel gear 110 that engages a second bevel 112 having an axis of rotation perpendicular to that of gear 110. Bevel gear 112 is mounted on a shaft 114 that passes through a circular opening in housing 102. The outer end of shaft 114 carries a tool head that includes a member 118 providing a square socket for engagement with the square head at the end of shaft 26. Secured to member 118 is a guide funnel 120 that can be placed around the square head of shaft 26 in order to easily guide that head into the socket provided by member 118. Then, when the user rotates the handle that is fixed to shaft 104 while holding housing 102 stationary, gear 112, shaft 114, member 118 and funnel 120 can be rotated in order to rotate shaft 26 and thus displace housing 18 relative to track 22.

Figure 4:
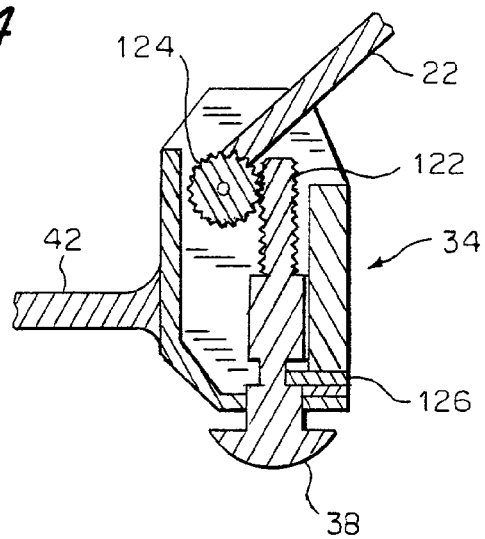
FIG. 4 is a cross-sectional view taken along a vertical plane, which can be the same plane as the view of FIG. 2, showing a worm gear displacement mechanism employed in the device of FIGS. 1A–1D.

FIG. 4 shows one exemplary embodiment of a rotational adjustment gear that may be provided in housing 34. The upper end of screw 38 is provided with a reduced diameter threaded portion 122 that engages teeth on gear wheel 124 to form a worm gear mechanism. Gear wheel 124 is pivotally mounted on housing 34. Screw 38 is provided with an annular recess into which is inserted a retaining pin 126 to prevent longitudinal movement of screw 38 relative to housing 34, while allowing screw 38 to rotate within housing 34. Rotation of screw 38 produces a corresponding rotation of gear wheel 124 about its pivot axis, thereby rotating track 22 relative to track 42.

It will be appreciated that the mechanisms shown in FIGS. 2, 3 and 4, as well as in FIG. 7, to be described below, are only exemplary. A variety of alternative mechanisms can easily be devised by those skilled in the mechanical mechanism arts.

The device shown in FIGS. 1 and 2 would be implanted in accordance with the procedure described below. Appropriate portions of the facial skeleton would be exposed surgically and the required osteotomy would be performed.

By way of example, this could be a Lefort I or II osteotomy. Plate 12 will be secured above the osteotomy separation by securing wing 14 to the anterior maxilla and securing wing 16 to the malar eminence and/or the zygomatic arch, using an appropriate number of bone screws in each case. As noted above, where possible or desired, various ones of extensions 72, 74 may be remove, by being broken off from strip 64, 66, before plate 12 is fastened in place.

Figure 5:
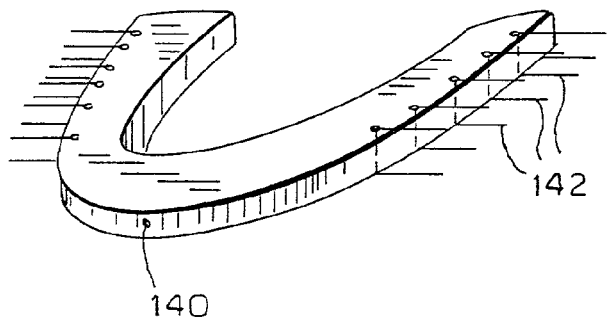
FIG. 5 is a perspective view showing a splint that may be used with the device of FIGS. 1A–1D.

Plate 60 will be secured to the upper jaw or the teeth, or to a splint that has been fabricated beforehand and that is secured to the upper teeth. FIG. 5 shows an occlusal splint 140 that was made by molding an acrylic material to a mold of the patient's upper teeth and then fitted securely thereto. A plurality of fixation wires 142 are embedded in splint 140. Wires 142 may be inserted through holes 62 in plate 60 and then twisted together in pairs in order to firmly secure plate 60 to splint 140.

Alternatively, orthodontic appliances may be affixed to the patient's upper teeth and provided with wires similar to wire 142 for fixation to plate 60.

Then, screw 38 is adjusted, if necessary, by the operating clinician to establish the desired angular relation between tracks 22 and 42. In this embodiment, screw 38 is accessible for subsequent adjustment by the clinician.

Thus, the entire device will be disposed internally, with housing 34, a portion of track 22, the entirety of track 42, housing 52 and shafts 26 and 56 disposed in the oral cavity. As a result, the device will not be readily observable and will subject the patient to minimum discomfort.

Subsequent to implantation, the spacing between plates 12 and 60 can be varied by the patient, or by a family member of the patient, simply by rotating shaft 26 and/or 56 according to the clinician's instructions, with appropriate hand tools.

In the illustrated embodiment, wings 14 and 16 are secured directly to housing 18 and extensions 64 and 66 are centered on a plane that passes approximately mid-way between the ends of housing 18 perpendicular to the longitudinal direction of track 22. This provides a desirable positioning with respect to the facial skeleton and a reliable connection between wings 14 and 16, on the one hand, and housing 18, on the other hand.

It will also be noted that in the embodiment shown in FIGS. 1A–1D, and particularly in FIG. 1B, housings 18, 34 and 52, tracks 22 and 46, shafts 26 and 56 and screw 38 are all centered on a common vertical plane. This provides a compact arrangement that results in reduced patient discomfort.

The embodiment illustrated in FIGS. 1A–1D allows a full range of adjustment in the spacing between plates 12 and 60 by allowing three different adjustments, two of which are linear and one of which is angular. After the device has been implanted, the spacing between plate 12 and 60 will be varied progressively and gradually as the osteotomy heals. However, for certain treatments, three adjustments may not be required. For example, the embodiment illustrated in FIGS. 1A–1D can be modified by fixing housing 18 to track 22 or forming those components as a single component, and/or by eliminating the rotational adjustment gear assembly and rigidly connecting tracks 22 and 42 together, or forming those tracks of a single piece. However, the advantage of the embodiment shown in FIGS. 1A–1D is that it offers the possibility of any combination of adjustments and thus provides a single model that will meet the needs of all mid-face distraction procedures.

A second embodiment of the invention is illustrated in FIGS. 6A–6D. Since this embodiment shares many of the features of the embodiment of FIGS. 1A–1D, only the difference is therebetween will be described.

Firstly, the embodiment of FIGS. 6A–6D includes an upper drive track 22' that differs from track 22 in that track 22' is linear, rather then having any right angle bends.

Upper housing 18 is associated with an elongated, flexible shaft 26' that corresponds functionally to shaft 26 of FIGS. 1A–1D. However, shaft 26' extends forwardly from housing 18 so as to be more readily accessible to a tool inserted from outside the patient's mouth. Track 42 is provided with a drive shaft guide 146, essentially in the form of a stirrup, to guide the free end of shaft 26'.

A rotation adjustment gear housing 34' is provided with a shaft 150 that allows the adjustment mechanism to be adjusted in the same manner as the other shafts. Thus, with this arrangement, the angle between tracks 22' and 42 can be adjusted subsequent to implantation, by the patient or an assistant, pursuant to instructions provided by the attending clinician.

Figure 7:
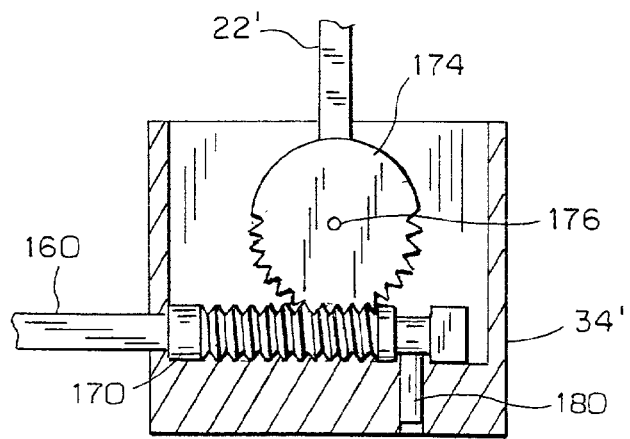
FIG. 7 is a cross-sectional, detail view of a component of the device of FIGS. 6A, 6B, 6C and 6D.
Figure 6C:
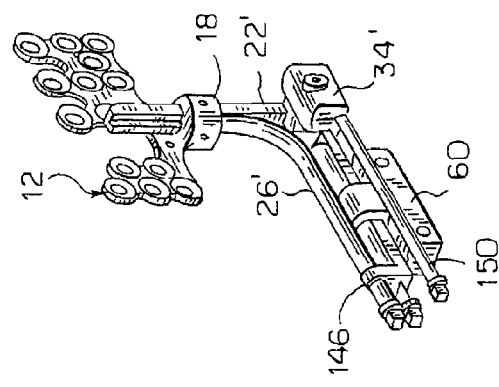
FIGS. 6A, 6B, 6C and 6D are, respectively, a side elevational view, a top plan view, a front perspective view and a rear perspective view of a second embodiment of a device according to the present invention.
Figure 6D:
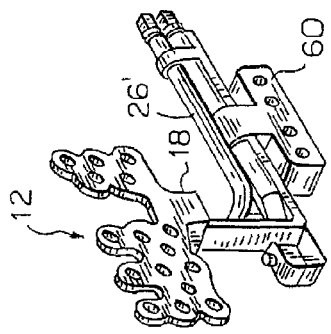
Figure 6A:
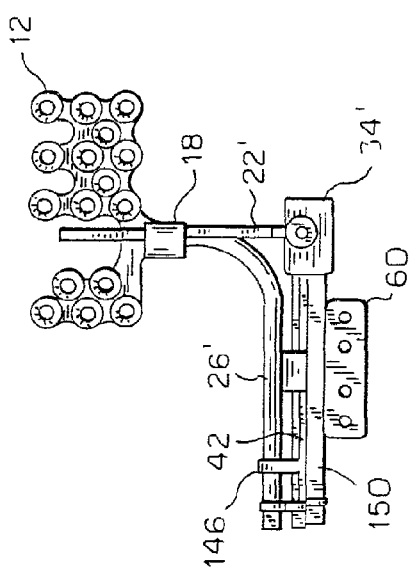
Figure 6B:
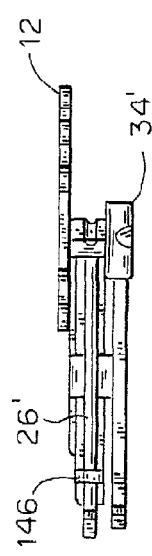
Figure 8:
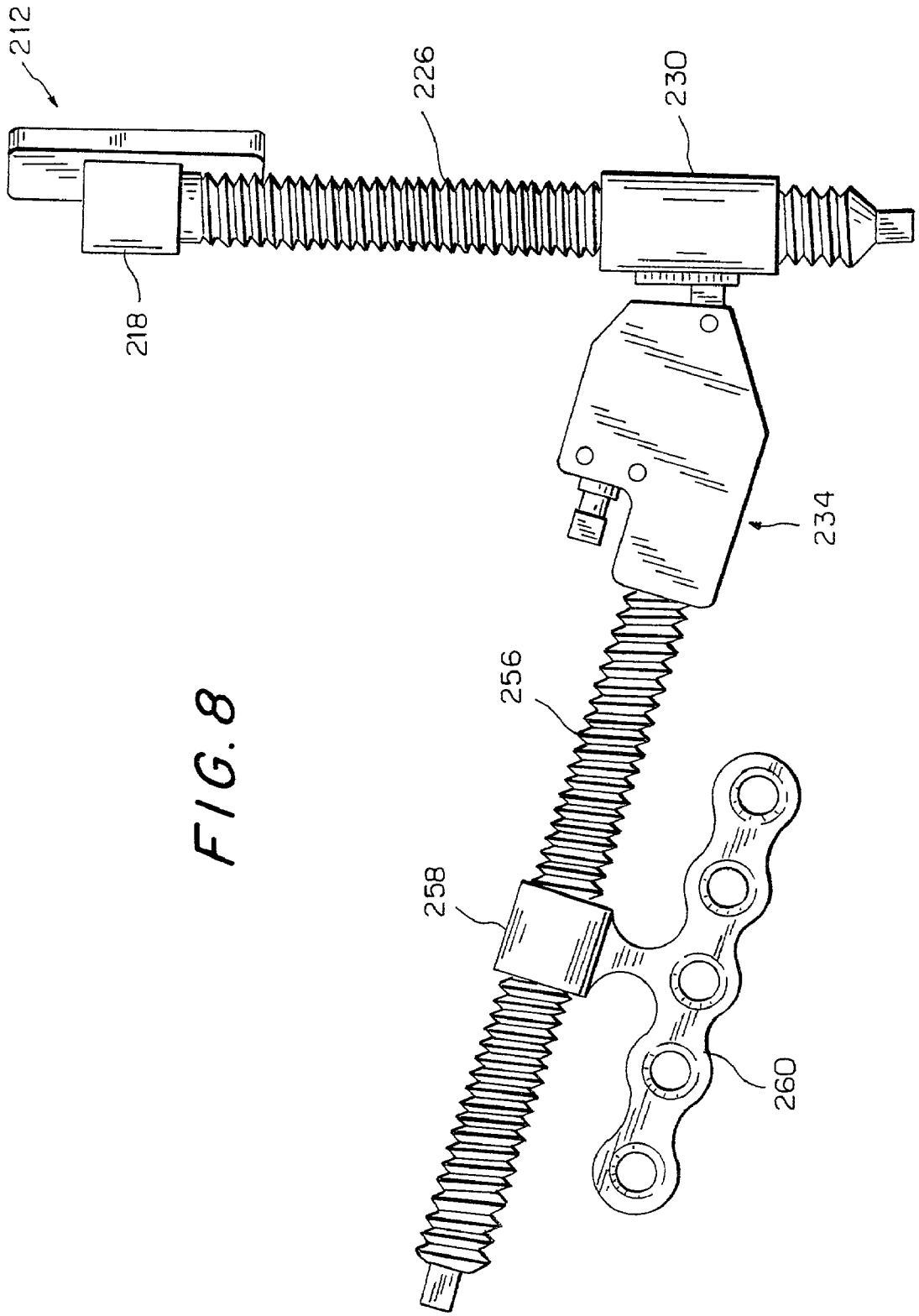
FIGS. 8, 9, 10 and 11 are, respectively, a side elevational view, a front elevational view, a bottom plan view and a side elevational, cross-sectional detail view of a third embodiment of a device according to the invention.
Figure 9:
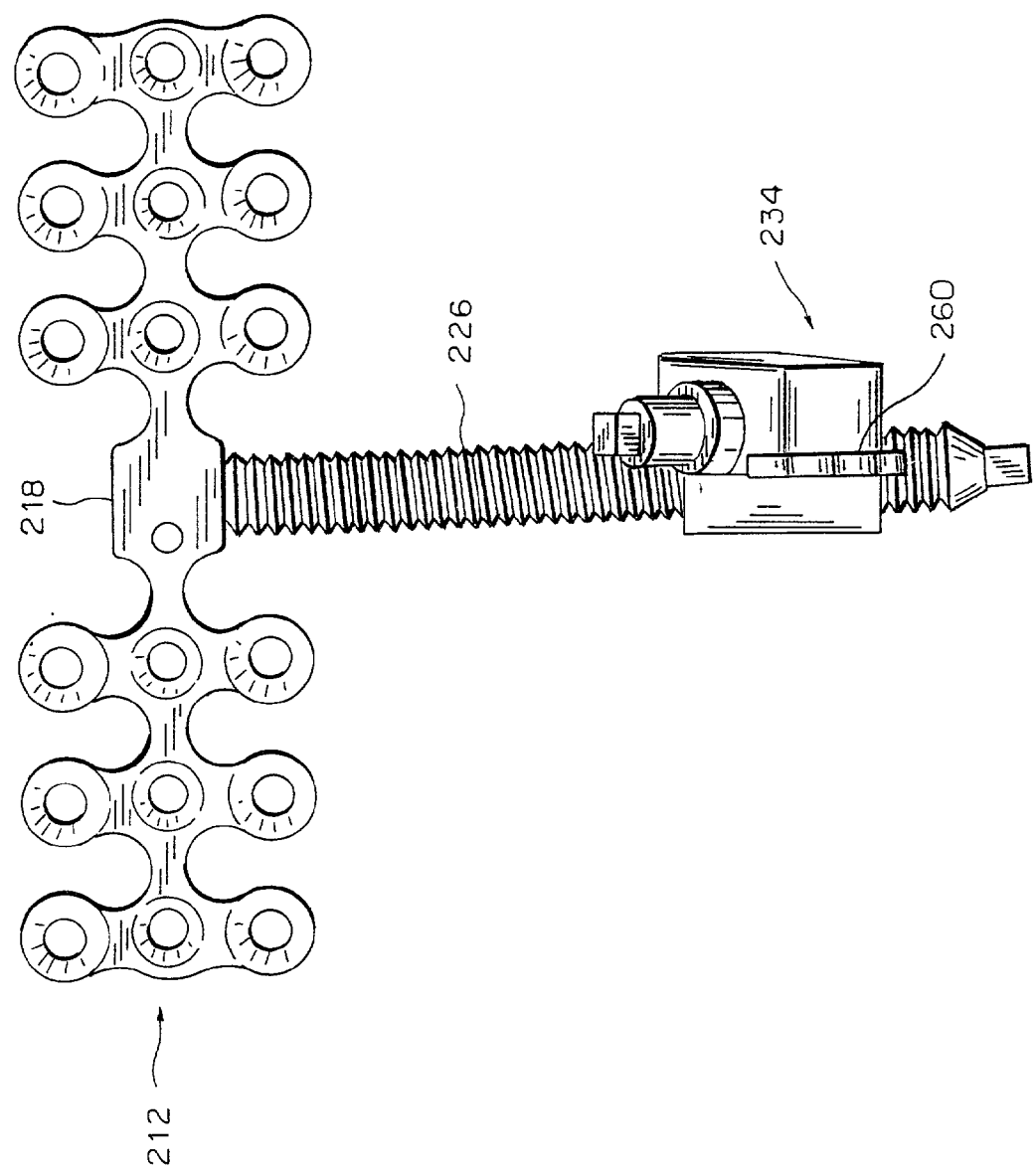
Figure 10:
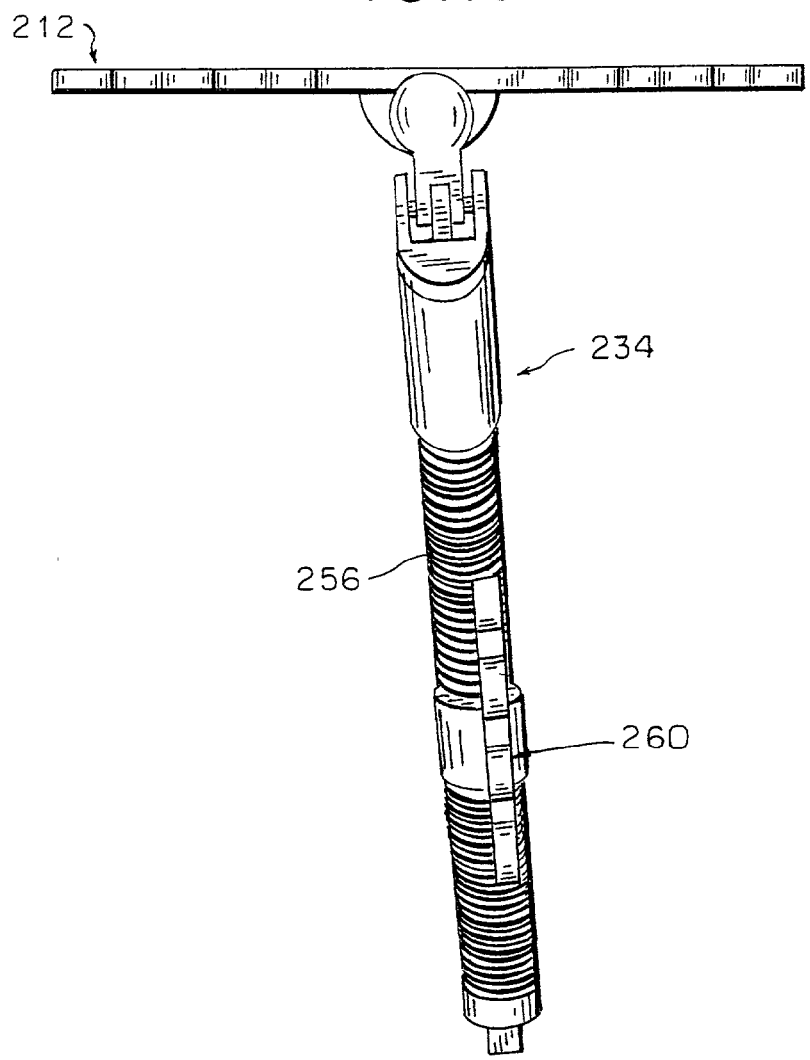

One suitable form of construction of the rotational adjustment gear in housing 34' is shown in FIG. 7.

In FIG. 7, one side of housing 34' has been removed to expose the interior thereof, which contains a screw, or threaded element, 170 secured to shaft 150 in order to rotate therewith. Housing 34' also contains a gear wheel 174 provided on at least a portion of its outer surface with gear teeth that will mesh with the thread of screw 170. Gear wheel 174 is fixed to housing 34' via a pivot shaft 176 and is secured to track 22'. Screw 170 is provided, at its distal end, with an annular groove in which a pin 180 is inserted to prevent movement of screw 170 in the direction of its longitudinal axis, while permitting screw 170 to be rotated with shaft 150. Rotation of shaft 150 and screw 170 produces a corresponding rotation of gear wheel 174 in order to vary the angular orientation of track 22' relative to track 42.

FIGS. 6A–6D also show an upper plate 12 that is shown only generally. In practical implementations of the device, plate 12 can have the structure and orientation shown in FIGS. 1A to 1D, or in FIGS. 1E and 1F. Lower plate 60 will be secured in the manner described above with reference to FIGS. 1A–1E.

The embodiment shown in FIGS. 1A–1D can be modified to include any one or more of these differing features of the embodiments shown in FIGS. 6A–6D.

A further embodiment of the invention is shown in FIGS. 8, 9, 10 and 11 and differs from the embodiments previously described essentially by the elimination of separate drive tracks and the connection of the various housings directly to threaded elements.

The basic components of this embodiment are an upper plate 212 composed of two wings and corresponding essentially to plate 12 of FIGS. 1A–1D, a housing 218 that forms a unit with plate 212, a threaded element 226 having an end secured in housing 218, an internally threaded sleeve 230 in threaded engagement with element 226, a housing 234 pivotally connected to sleeve 230, a threaded element 256 rotatably supported by housing 234, a sleeve 258 that is internally threaded and in threaded engagement with threaded element 256 and an anterior lower plate 260 that is secured to sleeve 258 and that corresponds to lower plate 60 of the embodiment shown in FIGS. 1A–1D.

Figure 11:
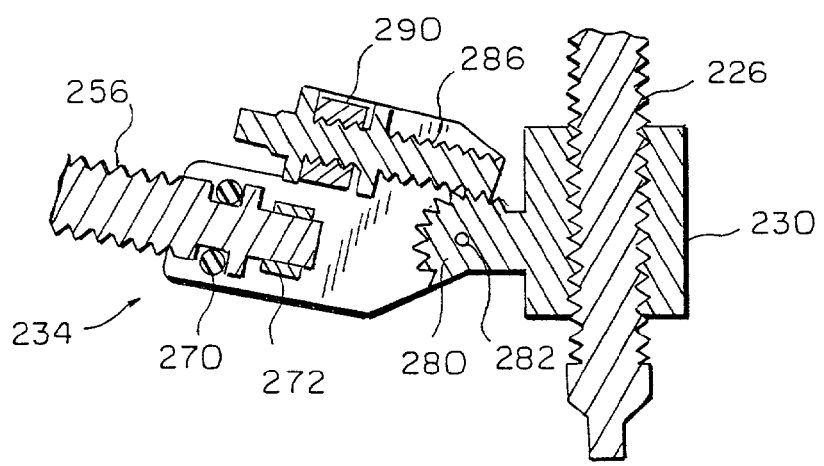

One possible form of construction of the interior of housing 234 is shown in FIG. 11. Threaded element 256 is supported by cylindrical bearings 270 and 272 that are fixed to housing 234 and that engage with recessed portions of threaded element 256 in order to allow threaded element 256 to be rotated about its axis, while being fixed against axial movement relative to housing 234.

Sleeve 230 carries a gear wheel segment 280 that is pivotally mounted to housing 234 at a pivot pin 282. Housing 234 further includes a threaded element 286 having a recessed portion via which threaded element 286 is retained in a cylindrical bearing 290 that is fixed to housing 234. The engagement between bearing 290 and threaded element 286 allows threaded element 286 to rotate about its axis while preventing axial movement of threaded element 286 relative to housing 234. The threads of threaded element 286 engage gear teeth on segment 280 so that rotation of element 286 will cause housing 234 to pivot relative to sleeve 230 about the axis of pivot 145 pin 282.

Rotation of threaded element 256 will produce a displacement of sleeve 258 and lower plate 260 along the axis of element of 256.

Threaded element 226 is retained in housing 218 by a structure that can be similar to components 270 and 272 shown in FIG. 11, whereby element 226 can rotate about its axis relative to housing 218, but is restrained from undergoing axial movement relative thereto. Thus, rotation of element 226 will produce a displacement of sleeve 230 along the axis of element 226.

The outer, or proximal, end of each element 226, 256 and 286 may be provided with a square head, similar to the square head 94 shown in FIG. 1C, that is engageable with a socket of a hand tool to allow the element to be rotated.

The embodiment illustrated in FIGS. 8–11 will be installed in the same manner as the embodiment of FIGS. 1A–D. At least threaded elements 256 and 286 can be rotated by insertion of a tool through the patient's mouth. Threaded element 226 might be rotated by the use of a special tool similar to that illustrated in FIG. 3.

Figure 12:
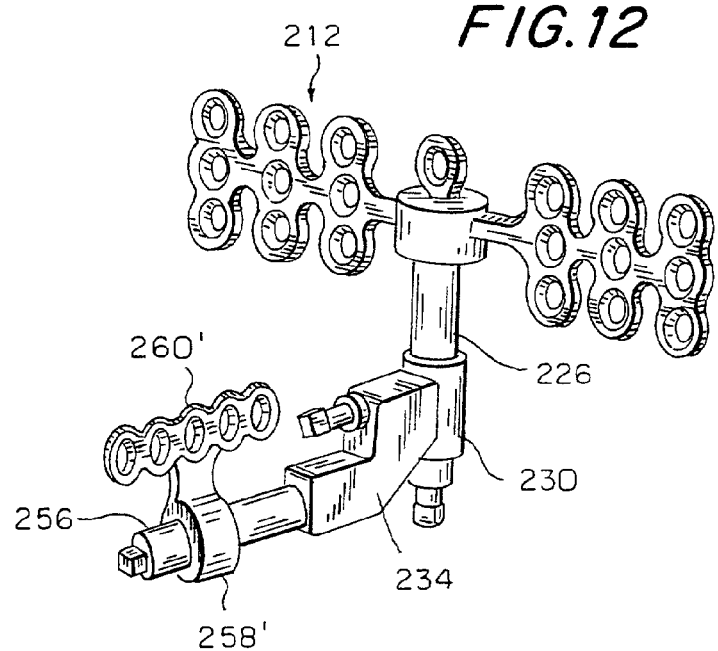
FIG. 12 is a perspective view showing a modified version of the embodiment of FIGS. 8–11.

FIG. 12 is a perspective view showing a modified version of the embodiment of FIGS. 8–11, which differs only in that anterior lower plate 260' is mounted above sleeve 258' in position to be fastenable to bone above the patient's upper teeth.

Figure 13:
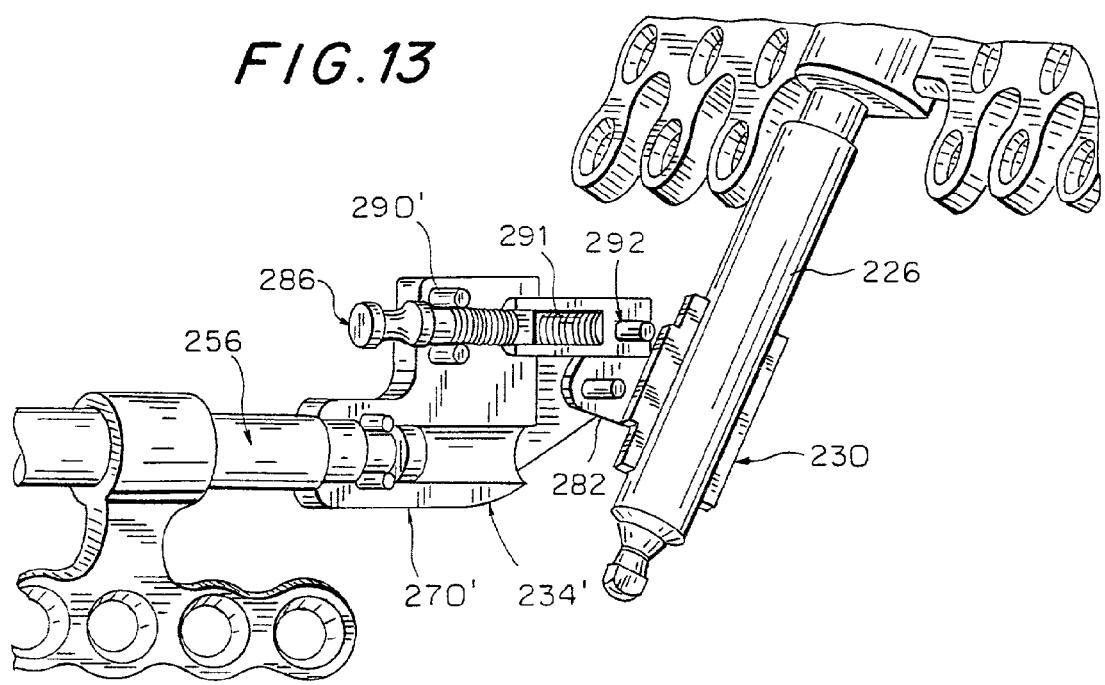
FIG. 13 is a perspective view, partly in cross section, of another modified version of the embodiment of FIGS. 8–11.

FIG. 13 shows another modified version of the embodiment of FIGS. 8–11. In the embodiment shown in FIG. 13, threaded element 256 is supported in a housing 234' by two pins 270' that engage at diametrically opposed sides of an annular recess in element 256 in order to allow threaded element 256 to be rotated about its axis, while being fixed against axial movement relative to housing 234'. Sleeve 230 is provided with two holes for receiving pivot pins 282 and 292. Housing 234' is pivotally mounted on pivot pin 282. Threaded element 286 is held in place in housing 234' by two pins 290' that engage at diametrically opposed sides of the annular recessed portion of element 256 that allow threaded element 256 to be rotated about its axis, while being fixed against axial movement relative to housing 234'. A connecting element 291 is pivotally mounted on pivot pin 292 and is provided with a bore having a female thread that mates with threaded element 286. Rotation of threaded element 286 causes element 286 to move axially relative to element 291, resulting in pivotal movement of housing 234' about pin 282. This causes element 256 to pivot relative to element 226.

Embodiments of the invention can be employed for performing segmental distraction of the alveolar ridge in order to close a cleft defect of alveolar bone and lower maxilla. For this purpose, subsequent to an osteotomy, a device according to the invention would be implanted in the manner described earlier herein and the anterior lower plate unit could be progressively advanced in the anterior direction during the course of bone regeneration at the osteotomy. This could be accompanied by a progressive vertical displace that increases the vertical spacing between the upper plate unit and the lower plate unit.

Devices according to invention can also be employed to effect vertical elongation of the alveolar ridge. In this case, after osteotomy, the lower plate unit can be secured to the alveolar ridge, at a location above and posterior to the patient's upper teeth, and progressive adjustments can be made to increase the vertical distance between the upper and lower plate units.

Devices according to the invention are well adapted for treatment of children whose adult teeth have not yet erupted, with lower plate 60 secured to an occlusal fixation splint.

The devices illustrated in the attached drawings will be implanted at the left side of the patient's face. In a complete mid-face distraction procedure, a device that is mirror symmetrical to those illustrated will be implanted in a mirror symmetrical manner at the right side of the patient's face.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:

1. A device for performing multi-directional internal distraction osteogenesis subsequent to a Lefort osteotomy, comprising:
   an upper plate unit configured to be secured to a portion of a patient's skull above the osteotomy;
   a lower plate unit configured to be secured to the patient's upper jaw or teeth at a location below the osteotomy; and
   an adjustment unit connecting said upper and lower plate units together and determining the position of said lower plate unit relative to said upper plate unit, wherein
   said adjustment unit is adapted to be located internally, and substantially within the patient's oral cavity, when said plate units are secured above and below the osteotomy, and
   said adjustment unit is operative to effect relative movement between said upper and lower plate units along a linear path, and pivotal movement between said upper and lower plate units, wherein said adjustment unit is operative to effect the relative movement along the linear path independently of the pivotal movement.

2. The device of claim 1, wherein said adjustment unit is manually controllable to vary the position of said lower plate unit relative to said upper plate unit.

3. The device of claim 2, wherein said adjustment unit comprises:
   an upper elongated member supporting said upper plate unit; and
   a lower elongated member supporting said lower plate unit, wherein
   each of said elongated members has a longitudinal axis, and
   the longitudinal axis of said upper elongated member extends in a direction transverse to the longitudinal axis of said lower elongated member.

4. The device of claim 3, wherein said upper elongated member has a portion that extends along a line which intersects said lower elongated member.

5. The device of claim 3, wherein said adjustment unit further comprises a coupling member connected between a lower end of said upper elongated member and a posterior end of said lower elongated member.

6. The device of claim 5, wherein said adjustment unit comprises at least one manually operable displacement mechanism for linearly displacing one of said plate units relative to said adjustment unit or angularly displacing said lower elongated member relative to said upper elongated member.

7. The device of claim 1, wherein said adjustment unit comprises at least one rotatably mounted elongated threaded element and at least one tubular, internally threaded element in threaded engagement with said at least one rotatably mounted elongated threaded element, and wherein said at least one rotatably mounted elongated threaded element is rotatable relative to said at least one tubular, internally threaded element for effecting a displacement of one of said plate units relative to the other one of said plate units.

8. The device as claimed in claim 1, wherein said adjustment unit is actuatable for effecting the movement along a linear path and the pivotal movement when the device is implanted in a patient.

9. The device as claimed in claim 1, wherein the pivotal movement effectuated by said adjustment unit is about an axis transverse to the linear path.

10. The device as claimed in claim 1, wherein said upper and lower plate units lie in mutually transverse planes.

11. A device for performing multi-directional internal distraction osteogenesis subsequent to a Lefort osteotomy, comprising:
    an upper plate unit configured to be secured to a portion of a patient's skull above the osteotomy;
    a lower plate unit configured to be secured to the patient's upper jaw or teeth at a location below the osteotomy; and
    an adjustment unit connecting said upper and lower plate units together and determining the position of said lower plate unit relative to said upper plate unit, wherein
    said adjustment unit is adapted to be located internally, and substantially within the patient's oral cavity, when said plate units are secured above and below the osteotomy, wherein:
    said adjustment unit is manually controllable to vary the position of said lower plate unit relative to said upper plate unit;
    said adjustment unit comprises:
       an upper elongated member supporting said upper plate unit; and
       a lower elongated member supporting said lower plate unit;
       each of said elongated members has a longitudinal axis, and the longitudinal axis of said upper elongated member extends in a direction transverse to the longitudinal axis of said lower elongated member;
    said adjustment unit further comprises a coupling member connected between a lower end of said upper elongated member and a posterior end of said lower elongated member;
    said adjustment unit comprises at least one manually operable displacement mechanism for linearly displacing one of said plate units relative to said adjustment unit or angularly displacing said lower elongated member relative to said upper elongated member, and
    said at least one displacement mechanism comprises a manually rotatable worm screw.

12. The device of claim 11, wherein one of said elongated members is provided with lateral groves and constitutes a rack that cooperates with said worm screw for effecting a linear displacement of the one of said plate units that is supported be said one of said elongated members.

13. The device of claim 11, wherein said at least one displacement mechanism comprises a first displacement mechanism coupled to said upper plate unit and a second displacement mechanism coupled to said lower plate unit.

14. The device of claim 13, wherein each of said elongated members is provided with lateral teeth and constitutes a rack that cooperates with said worm screw of a respective displacement mechanism for effecting a linear displacement of the respective one of said plate units that is supported by said respective displacement mechanism.

15. The device of claim 13, wherein said at least one displacement mechanism further comprises a third displacement mechanism that is an angular displacement mechanism associated with said coupling member, said third displacement mechanism including a gear wheel that supports one of said elongated members, is rotatable relative to the other one of said elongated members and cooperates with said worm screw to form a worm gear mechanism for effecting a relative rotation between said elongated members.

16. The device of claim 11, wherein each of said elongated members is provided with lateral teeth and constitutes a rack that cooperates with said worm screw of a respective displacement mechanism for effecting a linear displacement of the respective one of said plate units that is supported by said respective displacement mechanism.

17. A device for performing multi-directional internal distraction osteogenesis subsequent to a Lefort osteotomy, comprising:
    an upper plate unit configured to be secured to a portion of a patient's skull above the osteotomy;
    a lower plate unit configured to be secured to the patient's upper jaw or teeth at a location below the osteotomy; and
    an adjustment unit connecting said upper and lower plate units together and determining the position of said lower plate unit relative to said upper plate unit, wherein
    said adjustment unit is adapted to be located internally, and substantially within the patient's oral cavity, when said plate units are secured above and below the osteotomy, wherein:

said adjustment unit is manually controllable to vary the position of said lower plate unit relative to said upper plate unit;

said adjustment unit comprises:

an upper elongated member supporting said upper plate unit; and a lower elongated member supporting said lower plate unit;

each of said elongated members has a longitudinal axis, and the longitudinal axis of said upper elongated member extends in a direction transverse to the longitudinal axis of said lower elongated member;

said adjustment unit further comprises a coupling member connected between a lower end of said upper elongated member and a posterior end of said lower elongated member;

said adjustment unit comprises at least one manually operable displacement mechanism for linearly displacing one of said plate units relative to said adjustment unit or angularly displacing said lower elongated member relative to said upper elongated member, and said at least one manually operable displacement mechanism comprises a flexible, bendable shaft that is accessible from outside the patient's oral cavity after said device has been implanted to effect rotation of said shaft in order to perform a displacement.

18. A bone distractor for distracting bone tissue, the bone distractor comprising:

a first bone attachment portion;

a second bone attachment portion; and a linkage connecting the first bone attachment portion with the second bone attachment portion, the linkage allowing one of the first and second bone attachment portions to move with respect to the other one of the bone attachment portions along a linear path, and the linkage allowing relative pivotal movement to be effected between said first and second bone attachment portions, wherein said linkage is actuatable for effecting movement along the linear path and effecting the relative pivotal movement when said distractor is implanted in a patient.

19. The bone distractor as claimed in claim 18, wherein the first bone attachment portion is attachable to a first bone portion of a human skull, and the second bone attachment portion is attachable to a second bone portion of a human skull, wherein the first bone portion and the second bone portion may be parts of a maxilla of the human skull.

20. The bone distractor as claimed in claim 18 wherein each of said portions and said linkage comprises a modular element.

21. The bone distractor as claimed in claim 18, wherein said first and second bone attachment portions lie in mutually transverse planes.

22. The bone distractor as claimed in claim 18, wherein said linkage allows movement along the linear path to be independent of the relative pivotal movement.

23. A device for performing multi-directional internal distraction osteogenesis subsequent to a Lefort osteotomy, comprising:

an upper plate unit configured to be secured to a portion of a patient's skull above the osteotomy;

a lower plate unit configured to be secured to the patient's upper jaw or teeth at a location below the osteotomy; and an adjustment unit connecting said upper and lower plate units together and determining the position of said lower plate unit relative to said upper plate unit, wherein said adjustment unit is adapted to be located internally, and substantially within the patient's oral cavity, when said plate units are secured above and below the osteotomy, and said adjustment unit is operative to effect relative movement between said upper and lower plate units along a linear path, and pivotal movement between said upper and lower plate units, wherein said upper plate unit comprises:

an upper housing movable in an adjustment direction relative to said adjustment unit and having upper and lower ends that are spaced apart in the adjustment direction and two lateral sides that extend between said upper and lower ends; and an upper plate composed of two wings each extending from a respective lateral side in a direction transverse to the adjustment direction.

24. The device of claim 23, wherein each of said wings comprises a longitudinal strip that extends along a path between said upper and lower ends of said upper housing and is provided with a plurality of bone screw holes.

25. The device of claim 24, wherein at least one of said wings further comprises at least one extension that extends laterally from said strip and is provided with at least one further bone screw hole.

26. A bone distractor for distracting bone tissue, the bone distractor comprising:

a first bone attachment portion;

a second bone attachment portion; and a linkage connecting the first bone attachment portion with the second bone attachment portion, the linkage allowing one of the first and second bone attachment portions to move with respect to the other one of the bone attachment portions along a linear path, and the linkage allowing relative pivotal movement to be effected between said first and second bone attachment portions, wherein the relative pivotal movement allowed by said linkage is about an axis transverse to the linear path.

27. A device for performing multi-directional internal distraction osteogenesis subsequent to a Lefort osteotomy, comprising:

an upper plate unit configured to be secured to a portion of a patient's skull above the osteotomy;

a lower plate unit configured to be secured to the patient's upper teeth at a location below the osteotomy; and an adjustment unit connecting said upper and lower plate units together and determining the position of said lower plate unit relative to said upper plate unit, wherein said lower plate unit comprises: a lower plate; a splint constructed to be securely fitted to the upper teeth; and a plurality of fixation wires embedded in said splint and attachable to said lower plate.

* * * * *